(12) United States Patent
Hoffmann et al.

(10) Patent No.: US 8,518,403 B2
(45) Date of Patent: Aug. 27, 2013

(54) EXPRESSION-ENHANCED POLYPEPTIDES

(75) Inventors: Patrick Hoffmann, München (DE); Silke Mittelstrass, München (DE); Jens Hennecke, München (DE); Tobias Raum, München (DE)

(73) Assignee: Amgen Research (Munich) GmbH, Munich (DE)

( * ) Notice: Subject to any disclaimer, the term of this patent is extended or adjusted under 35 U.S.C. 154(b) by 1327 days.

(21) Appl. No.: 11/572,116

(22) PCT Filed: Jul. 15, 2005

(86) PCT No.: PCT/EP2005/007748
§ 371 (c)(1),
(2), (4) Date: Oct. 8, 2008

(87) PCT Pub. No.: WO2006/008096
PCT Pub. Date: Jan. 26, 2006

(65) Prior Publication Data
US 2009/0053223 A1 Feb. 26, 2009

(30) Foreign Application Priority Data
Jul. 16, 2004 (EP) .................................... 04016890

(51) Int. Cl.
*C12P 21/04* (2006.01)
*C12P 21/08* (2006.01)
*C12N 15/00* (2006.01)
*C12N 15/62* (2006.01)
*C12N 15/64* (2006.01)
*A61K 39/395* (2006.01)

(52) U.S. Cl.
USPC ................ 424/133.1; 424/135.1; 424/136.1; 424/137.1; 424/138.1; 424/141.1; 424/144.1; 424/154.1; 424/156.1; 424/173.1; 424/174.1; 424/179.1; 435/69.6; 435/69.7; 435/455; 530/387.3; 530/387.5; 530/387.7; 530/388.1; 530/388.22; 530/388.7; 530/388.75; 530/388.8; 530/388.85; 530/391.1

(58) Field of Classification Search
None
See application file for complete search history.

(56) References Cited

U.S. PATENT DOCUMENTS

| | | | | | |
|---|---|---|---|---|---|
| 5,013,653 | A | * | 5/1991 | Huston et al. | 435/69.7 |
| 5,739,277 | A | | 4/1998 | Presta et al. | 530/326 |
| 5,932,448 | A | * | 8/1999 | Tso et al. | 435/69.6 |
| 2003/0044423 | A1 | | 3/2003 | Gillies et al. | 424/192.1 |
| 2004/0018586 | A1 | | 1/2004 | Rosendahl et al. | 435/68.1 |
| 2005/0255115 | A1 | * | 11/2005 | Huang et al. | 424/155.1 |
| 2011/0020329 | A1 | * | 1/2011 | King et al. | 424/133.1 |

FOREIGN PATENT DOCUMENTS

| | | | |
|---|---|---|---|
| WO | WO 01/04135 | | 1/2001 |
| WO | WO01/95919 | * | 12/2001 |
| WO | WO01/95942 | * | 12/2001 |
| WO | WO03/004648 | * | 1/2003 |
| WO | WO03/040695 | * | 5/2003 |

OTHER PUBLICATIONS

Glombik et al (EMBO Journal, 1999, vol. 18, pp. 1059-1070).*
Yang et al, Protein Engineering, 2003, vol. 16, pp. 761-770.*
Marty et al., "Production of functionalized single-chain Fv antibody fragments binding to the ED-B domain of the B-isoform of fibronectin in *Pichia pastoris*," *Protein Expression and Purification*, 21:156-164, 2001.
Yang et al., "Tailoring structure-function and pharmacokinetic properties of single-chain Fv proteins by site-specific PEGylation," *Protein Eng.*, 16(10):761-70, 2003.
Albrecht et al., "Production of soluble ScFvs with C-Terminal-Free thiol for site-specific conjugation or stable dimeric ScFvs on demand," *Bioconjug. Chem.*, 15:16-26, 2004.
Luo et al., "An engineered bivalent single-chain antibody fragment that increases antigen binding activity," *J. Biochem.*, 121:831-834, 1997.
Olafsen et al., "Covalent disulfide-linked anti-CEA diabody allows site-specific conjugation and radiolabeling for tumor targeting applications," *Protein Eng. Des. Sel.*, 17:21-27, 2004.
Stevenson et al., "Conjugation of human Fcgamma in closed-hinge or open-hinge configuration to Fab'gamma and analogous ligands," *J. Immunology*, 158:2242-2250, 1997.
Volkel et al., "Targeting of immunoliposomes to endothelial cells using a single-chain Fv fragment directed against human endoglin (CD105)," *Biochim. Biophys. Acta.*, 1663:158-166, 2004.
Li et al., "Construction and expression of an eukaryotic expression vector to humanized sifulfied-stabilized anti-HCC scFv-$CD_3\zeta$," *Chin. J. Cancer Prev. Treat.*, 11(4):337-340, 2004.

* cited by examiner

*Primary Examiner* — Karen Canella
(74) *Attorney, Agent, or Firm* — Marshall, Gerstein & Borun LLP

(57) ABSTRACT

A composite polypeptide, said composite polypeptide comprising a desired polypeptide and an expression enhancing domain ("EED"), said EED comprising first and second cysteine amino acid residues Cys1 and Cys2, respectively, Cys1 being located closer to the N-terminus of the composite polypeptide molecule than Cys2, wherein Cys1 and Cys2 are separated by a polypeptide linker, said linker—being free of cysteine and proline;—defining a length sufficient to allow Cys1 and Cys2 to engage in an intramolecular disulfide bond with one another; and—having a flexible polypeptide conformation essentially free of secondary polypeptide structure in aqueous solution, wherein at least one of Cys1 and Cys2 is derivatized with a derivatization moiety.

22 Claims, 6 Drawing Sheets

1. scFv with C-terminal (His)6-Pro tag
2. scFv with C-terminal (His)6-Pro tag
3. scFv with C-terminal (His)6-Cys-Pro tag
4. scFv with C-terminal (His)6-Cys-Pro tag
5. scFv with C-terminal (His)6-Cys-(Gly)4-Cys-Pro tag
6. scFv with C-terminal (His)6-Cys-(Gly)4-Cys-Pro tag 1. Monomer fraction of scFv with C-terminal (His)6-Cys-Pro tag
2. Dimer fraction of scFv with C-terminal (His)6-Cys-Pro tag
3. Monomer fraction of scFv with C-terminal (His)6-Cys-(Gly)4-Cys-Pro tag
4. Dimer fraction of scFv with C-terminal (His)6-Cys-(Gly)4-Cys-Pro tag 1. scFv with C-terminal (His)6-Cys-Pro tag blocked with Ethylmaleimide
2. scFv with C-terminal (His)6-Cys-(Gly)4-Cys-Pro tag blocked with Ethylmaleimide
3. scFv with C-terminal (His)6-Cys-Pro tag conjugated with PEG 20kD Maleimide
4. scFv with C-terminal (His)6-Cys-(Gly)4-Cys-Pro tag conjugated with PEG 20kD Maleimide

EXPRESSION-ENHANCED POLYPEPTIDES

This application is a national phase application under 35 U.S.C. §371 of International Application No. PCT/EP 2005/007748 filed 15 Jul. 2005, which claims priority to European Patent Application No.: EP 04 016 890.8 filed 16 Jul. 2004. The entire text of each of the above-referenced disclosures is specifically incorporated herein by reference without disclaimer.

The invention relates to polypeptide molecules which have been modified to improve their expression characteristics. The modified polypeptide molecules are expressed in better/higher yields than their corresponding partners, i.e., polypeptide molecules that have not been modified (on the nucleic acid level). The invention further relates to compositions comprising such polypeptides. Finally, the invention provides a method to prepare the modified polypeptide molecules mentioned previously. Throughout the following description, mention of a (composite) polypeptide is to be understood as implying both the polypeptide per se and, where appropriate, the corresponding nucleic acid sequence, as will be appreciated by the skilled reader. The same applies for the (desired) polypeptide and the expression-enhancing domain (EED).

Expression of recombinant polypeptides in microbial host systems is an efficient way of producing large amounts of a desired polypeptide. When the polypeptide produced is intended for use as a diagnostic and/or therapeutic agent, further modification of the polypeptide as expressed is often necessary. For example, a polypeptide intended for use as a diagnostic agent might need to be modified such that it can bind to a solid support. Alternatively, the polypeptide may need to be coupled to an agent allowing it to be visualized by a certain imaging method. A polypeptide intended for administration to a patient as part of a course of therapy may need to be modified in order to modulate its in vivo properties, for example its pharmacokinetic properties.

Derivatization of a recombinantly produced polypeptide is most often accomplished by chemical reaction between a chemical substance ("derivatization moiety") and a reactive side group of one or more of the amino acids comprised within the polypeptide. The result is a covalent coupling of the derivatization moiety to the polypeptide, wherein the location and valency of such coupling(s) is dictated by the respective location and number of reactive amino acids within the polypeptide. This means that in a polypeptide with multiple reactive amino acids, chemical coupling of a derivatization moiety with the polypeptide will occur multiple times at locations throughout the polypeptide corresponding to the locations of the reactive amino acids.

For some purposes, such a multivalent, site-nonspecific coupling of derivatization moieties to a polypeptide may be desirable, but more often it is not. For example, in a diagnostic procedure, it may be important for accurate quantification of measurements to limit the number of derivatizations per polypeptide molecule to one. Similarly, successful therapeutic use of a polypeptide in vivo often hinges on the ability of the medical practitioner to precisely predict and control the biological activity of this polypeptide. In such a situation, variations resulting from uncontrolled and site-nonspecific derivatization of the polypeptide used may understandably be inconsistent with the intended course of therapy. In addition, a site-nonspecific coupling of a therapeutic or diagnostic polypeptide with a derivatization moiety may lead to an impairment of the polypeptide's desired activity. This might for example be the case when a single chain antibody polypeptide is derivatized in a site-nonspecific fashion such that the antigen binding site is sterically and/or electrostatically prevented from binding to antigen or reduced in its binding activity. In such a case, the desired therapeutic or diagnostic effect of the single chain antibody may be abolished or at least attenuated.

It is often desirable, then, to engineer recombinant polypeptides such that derivatization is possible only at predefined locations, or only at one predefined location in the polypeptide molecule. The valency of coupling can be tuned by controlling the number of reactive amino acids in the polypeptide, and the desired polypeptide activity and/or chemical characteristics may be modulated by planning the location of such couplings so as not to physically impair the interaction of the polypeptide with other molecules in the environment.

One amino acid which has proven useful in this regard is cysteine. Because of its importance in stabilizing protein structure via formation of disulfide bonds, cysteine normally occurs in polypeptides only at defined locations. By incorporating a single cysteine into a "benign" region of the polypeptide not directly required for the desired polypeptide activity, one can take advantage of cysteine's reactive sulfhydryl side chain as a natural anchor point for a desired derivatization without, or without significantly affecting the desired polypeptide activity (Volkel T., et al. (2004) Biochim Biophys Acta 1663, 158-66).

However, incorporation of additional cysteine residues into polypeptides for purposes of derivatization entails certain disadvantages. Often, the desired polypeptide will already have cysteine residues in its amino acid sequence for the purposes of structural stabilization. An additional cysteine incorporated for the purpose of derivatizing the polypeptide with a derivatization moiety may in this case enter into undesirable disulfide linkages with such already present cysteines, severely perturbing the polypeptide structure necessary for a desired activity.

Even if the desired polypeptide does not itself contain any cysteine residue in its amino acid sequence, the incorporation of a single cysteine residue can still lead to problems. Following expression in a host organism, polypeptides containing an engineered cysteine amino acid residue can form polypeptide dimers with one another via intermolecular disulfide bonds between the thiol (i.e. sulfhydryl) groups of the two cysteine residues in the respective polypeptides (Albrecht H., et al. (2004) Bioconjug Chem 15, 16-26; Olafsen T., et al. (2004) Protein Eng Des Sel 17, 21-7). This danger is particularly large when using prokaryotic expression systems to produce the polypeptide. This is because in such systems, proteins are gradually transported into the periplasmatic space of the microbial host, where oxidative conditions prevail While such oxidative conditions are essential for the formation of desirable, structure-stabilizing disulfide bonds in the nascent polypeptide chain, they also promote the formation of undesirable intermolecular disulfide bonds between free cysteine residues intended as later derivatization points in two respective polypeptides.

The above issues are not limited to expression in prokaryotes. In Luo et al. (1997) J Biochem 121, 831-4, experiments were described comparing the amount of yeast-expressed monomeric and dimeric (i.e. linked via an intermolecular disulfide bond) scFv polypeptide depending on whether this scFv polypeptide comprised one or two C-terminal cysteine residues. It was found that scFv with a single C-terminal cysteine residue was more likely to exist in dimeric form, while scFv with two C-terminal cysteine residues was more likely to exist in monomeric form. It is also apparent from this publication that the total amount of expressed polypeptide remains about the same, irrespective of the isoform distribution. Additionally, it is revealed that the construct that has two cysteine residues (which exhibits a tendency to form an intramolecular disulfide bond) exhibits only poor binding activity.

Especially when expressing polypeptides intended for therapeutic use, it is often important for reasons of product homogeneity to produce the monomeric rather than the dimeric isoform. The prior art, embodied by the above mentioned publication of Luo et al., then, provides the researcher interested in expressing a monomeric polypeptide derivatizable at cysteine with certain tools to achieve this end. However, the prior art does not provide for a tool suitable to express the (monomeric) isoform in acceptable amounts and with acceptable binding activity. Thus, it was an object of the present invention to develop a DNA construct allowing high yield expression of the corresponding polypeptide exhibiting an acceptable binding activity, wherein the polypeptide is predominantly obtained as a monomeric polypeptide.

The inventors have solved this object by providing a nucleic acid encoding a so-called composite polypeptide according to the present invention, as defined in the claims. The nucleic acid, if appropriately expressed, provides for a composite polypeptide, said composite polypeptide comprising a desired polypeptide and an expression enhancing domain ("EED"), said EED comprising first and second cysteine amino acid residues Cys1 and Cys2, respectively, Cys1 being located closer to the N-terminus of the recombinant polypeptide molecule than Cys2, wherein Cys1 and Cys2 are separated by a polypeptide linker, said linker
  being free of cysteine and proline;
  defining a length sufficient to allow Cys1 and Cys2 to engage in an intramolecular disulfide bond with one another; and
  having a flexible polypeptide conformation essentially free of secondary polypeptide structure in aqueous solution,
wherein at least one of Cys1 and Cys2 is derivatized with a derivatization moiety.

By incorporating not one but two cysteine residues Cys1 and Cys2 into the EED and by tuning the length and specifying the nature of the polypeptide linker sequence disposed therebetween to promote formation of an intramolecular disulfide bond between Cys1 and Cys2, such a disulfide bond forms, rendering Cys1 and Cys2 unable to participate in unwanted inter—or intramolecular disulfide bridges as described above. In a sense, each of Cys1 and Cys2 become the respective other's protective group. When an intramolecular disulfide loop has been formed between Cys1 and Cys2, Cys2 may be seen as the derivatizing moiety of Cys1. Conversely, Cys1 may be seen as the derivatizing moiety of Cys2.

Composite polypeptides which have been engineered, at the nucleic acid level, to contain two cysteine residues as described above have the advantage that they bear chemical anchor points for later (i.e. post-expression and -isolation) derivatizations. At the same time, the danger of formation of unwanted intermolecular disulfide linkages is drastically reduced, as such danger would in this case arise mainly from other cysteine residues present in the desired polypeptide for the (desirable) disulfide stabilization of polypeptide structure. Such disulfide bonds normally form in an oxidative environment during and/or following translation as the nascent polypeptide gradually grows. As such, any free sulfhydryl group of a cysteine needed for the stabilization of polypeptide structure normally finds its disulfide partner relatively quickly and is thus blocked from further unwanted reactions. The incorporation of a linker optimized in length, chemical and steric properties to allow Cys1 and Cys2 to form a mutual disulfide bond ensures that Cys1 and Cys2 will react only with one another and not with a spatially distant cysteine residue in the polypeptide which is needed for stabilization of polypeptide structure, but which has not yet reacted with its intended counterpart cysteine residue. In short, the linker ensures that Cys1 and Cys2 will always be closer to one another than either Cys1 or Cys2 is to any other cysteine residue in the polypeptide.

Once expressed and isolated, such a composite polypeptide exhibiting a disulfide bond between Cys1 and Cys2 may be exposed to reducing conditions sufficient to open (only) the disulfide linkage between Cys1 and Cys2. Following this, derivatization of Cys1 and/or Cys2 with derivatization moieties other than the respective other Cys1 or Cys2 may be performed.

In addition to the advantage of obtaining a derivatized polypeptide (which can be rederivatized following isolation) without the disadvantages described above, it has also surprisingly been found that polypeptides which have been engineered to comprise an EED (i.e., composite polypeptides within the meaning of the invention) also exhibit higher levels of overall expression from their corresponding nucleic acids as compared to polypeptides which do not comprise an EED. While the composite polypeptide according to the invention may be expected to result in less unwanted dimer than a polypeptide without the EED, it is entirely unexpected based on the teaching in the prior art (e.g., the publication of Luo et al., cited above) that the overall expression of total polypeptide with acceptable binding activity would be increased by incorporation of the EED according to the present invention. The composite polypeptide of the invention, then, can be produced in overall higher yield as compared to the desired polypeptide without EED, wherein the ratio of monomeric composite polypeptide relative to dimeric composite polypeptide is increased relative to the ratio seen in production of the desired polypeptide lacking an EED. In this way, monomeric polypeptide is not only favored over dimeric polypeptide, but the overall higher amount of polypeptide results in much more (over 5-fold more) monomeric polypeptide which can then be (re-)derivatized as needed.

Without being bound by theory, the inventors believe that the surprising increase in total expressed polypeptide observed is due at least in part to the propensity of Cys1 and Cys2 within the EED to form a disulfide bond with one another. To explain why this is believed to be so, it is helpful to consider what happens during the subsequent expression of two identical polypeptides which do not comprise an EED as defined above. For the purposes of the foregoing discussion, these identical polypeptides will be referred to as PP1 and PP2, and each comprises the same desired polypeptide as well as a portion C-terminal thereto with only one cysteine residue (i.e. neither PP1 nor PP2 comprises an EED as defined above). The descriptors 1 and 2 denote, then, not different polypeptide identities, but rather the chronological order in which identical polypeptides are expressed.

Considering now that PP1 is expressed before PP2, it (PP1) will gradually be transported into an oxidative cellular environment in the direction N-->C, meaning that the amino terminus—that of the desired polypeptide—will be the first end to emerge into said oxidative environment. Emerging in this way, a cysteine residue within the desired polypeptide which will participate in a structure-stabilizing disulfide bond need only wait for its partner cysteine residue, the latter being located more towards the C-terminal end of the desired polypeptide—to emerge into the oxidative environment for said disulfide bond to form. This process continues as the desired polypeptide continually emerges, until all disulfide bonds necessary for structural stabilization within the desired polypeptide have been formed. Once the desired polypeptide component of PP1 has completely emerged (and properly folded), the C-terminal portion of PP1 with only one cysteine residue emerges. However here, there exists no partner cysteine with which this single cysteine may react to form a disulfide bond, so this single cysteine residue remains unpaired. Once the finished PP1 has been released, then, the desired polypeptide portion of PP1 is properly folded and disulfide-stabilized, and the C-terminal portion of the molecule bears one cysteine residue with a reactive sulfhydryl group.

Considering now that PP2 begins to be expressed into the same environment in which the completed PP1 resides, the N-terminal end of PP2 will first emerge. The first cysteine residue within the desired polypeptide portion of PP2 emerges but cannot yet form the intended structure-stabilizing disulfide bond since its cysteine reaction partner within the desired polypeptide portion of PP2 has not yet emerged. However, the single, unpaired cysteine residue within the desired polypeptide portion of PP2 may react with the single, unpaired cysteine residue in the C-terminal portion of the already completed PP1. In this way, an unwanted disulfide bond is formed between the first cysteine residue within the desired polypeptide portion of PP2 and the unpaired cysteine residue in the C-terminal portion of PP1. In such a scenario, the second cysteine residue in the desired polypeptide portion of PP2 would react with the unpaired cysteine residue in the C-terminal portion of PP2, or another cysteine residue within the desired polypeptide portion of PP2. Either way, the array of resulting disulfide bonds will very likely result in an improperly assembled polypeptide complex devoid, or substantially devoid of the biological activity of the desired polypeptide.

Such an improperly assembled polypeptide is likely to be recognized as such and degraded by intracellular proteinases, thus reducing the amount of total polypeptide obtained. In the event that such an improperly assembled polypeptide is not actively degraded in this manner, it is likely to exist as an insoluble aggregate with other malformed polypeptides of this type, and would be removed from properly assembled polypeptide in the course of standard polypeptide isolation procedures. In any event, polypeptide which is improperly assembled in this manner will tend to lower the amount of properly assembled polypeptide finally obtained in standard polypeptide isolation procedures.

In contrast, a composite polypeptide according to the invention comprises not only two cysteine residues (Cys1 and Cys2) in an EED, but also a linker disposed therebetween, said linker having been optimized to promote disulfide bond formation between Cys1 and Cys2. In light of the above considerations regarding PP1 and PP2, and supposing now that PP1 and PP2 are composite polypeptides according to the invention (i.e. they each comprise an EED), it is clear that neither Cys1 nor Cys2 in each of the respective EEDs will remain unpaired, since Cys1 and Cys2 within a respective EED will have formed a disulfide bond with one another. Improperly assembled polypeptides are avoided, having the effect that the products are not degraded by intracellular proteinases and/or do not form aggregates. As a result, the amount of composite polypeptide expressed and isolated is greatly increased.

In summary, then, the expression of the composite polypeptide according to the invention results in an increase in the monomer:dimer ratio of polypeptide. At the same time, the levels of overall polypeptide obtained—regardless of the isoform of the polypeptide—are also increased relative to a polypeptide lacking the EED as defined above. The net result is that a very small amount of dimeric and/or multimeric polypeptide and a vastly larger amount of monomeric polypeptide is obtained with a composite polypeptide comprising the EED as described above than is observed for comparative desired polypeptides in which an EED as defined above is lacking.

Within the meaning of the present invention, "N-terminus" and "C-terminus" are to be understood according to established convention in biochemistry: The N-terminus of a polypeptide is the end of the polypeptide chain ending in an amino group, while the C-terminus of a polypeptide is the end of the polypeptide chain ending in a carboxyl group. The fact that Cys1 is located closer to the N-terminus than Cys2 establishes the orientation of Cys1 and Cys2 relative to one another within the polypeptide chain. By this, the orientation of the EED in which Cys1 and Cys2 are comprised is also established.

Within the meaning of this embodiment of the invention, a polypeptide linker with a "flexible polypeptide conformation" is a polypeptide linker having at each covalent bond within the polypeptide chain sufficient degrees of rotational freedom to render the polypeptide linker as a whole largely unrestricted, i.e. restricted only by its length, in the conformations it may assume within three-dimensional space. As such, imagining a polypeptide linker anchored at one end at an imaginary point in three-dimensional space and defining a sphere around this point with a radius corresponding to the length of the fully extended polypeptide linker, if the polypeptide linker has a "flexible polypeptide conformation", the distal end of this polypeptide linker (i.e. the free, non-anchored end) must be able to touch any point in three-dimensional space located on or within said sphere with equal ease. This model gives rise to the corollary that such a polypeptide linker with "flexible polypeptide conformation" must also be "essentially free of secondary polypeptide structure", for example of stretches of alpha-helix or beta-sheet. Any predisposition of the polypeptide linker toward a motif of polypeptide secondary structure will necessarily limit the degree of spatial freedom enjoyed by the linker's free end, thereby constraining this end with regard to the points it is able to reach within the sphere defined above. This flexibility contributes to the ability of the linker to double back on itself, thereby allowing Cys1 and Cys2 to form an intramolecular disulfide linkage.

Undesired secondary structure may be ordered (as in the case of the alpha-helix and beta sheet described above) or may be disordered, as would be expected if, say, a proline residue were to exist in the linker sequence (the constrained ring in proline is known to cause kinks in the polypeptide backbone). Without being bound by theory, the inventors believe that this intrinsic flexibility of the linker between Cys1 and Cys2 is a major determinant in ensuring the formation of a disulfide bond between these two cysteine residues, and that efficient disulfide bond formation is linked to the marked enhancement of overall polypeptide expression observed (see reasons as set out above). For this reason it is important to avoid including amino acids such as proline in the sequence of the linker, since such incorporation restricts the free movement of the linker necessary to allow Cys1 and Cys2 to migrate into one another's vicinity such that the desired disulfide bond forms. Amino acid residues that are allowed in the linker according to the present invention comprise, but are not limited to, Gly, Ala, Val, Leu, Ile, Ser, Thr, Met, Tyr, Asn, Gln.

Within the meaning of the present invention, the term "derivatized" is to be understood as describing a situation in which one or both of the amino acid residues Cys1 and Cys2 have entered into reaction with a "derivatization moiety". A derivatization moiety may for example be a compound comprising a maleimide group, for example a PEG molecule comprising a maleimide group. In this particular exemplary, non-limiting case, the resulting derivatized Cys1 and/or Cys2 will have been derivatized with a PEG molecule via a covalent S-C bond resulting from nucleophilic attack by the sulfur atom in Cys1 and/or Cys2 with one of the unsaturated carbon atoms within the maleimide ring. As another example, a "derivatization moiety" may also be a molecule which itself comprises a sulfhydryl group, so that the resulting derivatized Cys1 and/or Cys2 will have been derivatized with this molecule via a covalent S-S, i.e. disulfide, bond. It is within the meaning of "derivatized" that Cys1 and/or Cys2 can react with another cysteine residue in the same or another polypeptide chain. Specifically, the formation of the desired intramolecular disulfide bridge between Cys1 and Cys2 as described above is to be understood as falling within the meaning of "derivatized" in the present invention; in this case, Cys1 will have been derivatized by Cys2, and vice versa. Generally, then, from the standpoint of Cys1, "derivatized" covers all scenarios in which Cys1 has participated in a covalent chemical reaction with a species other than itself (e.g. with Cys2). Likewise, "derivatized" also covers all scenarios in which Cys2 has participated in a covalent chemical reaction with a species other than itself (e.g. with Cys1).

According to a preferred embodiment of the invention, at least 75% of the amino acid residues in the. linker are selected from Gly, Ala, Val, Leu, Ile, Ser, Thr, Met, Tyr, Asn, and Gln.

Most preferred are Gly, Ser, Ala and Thr. These amino acids are either uncharged, are well or reasonably well soluble in water, or are both.

According to a preferred embodiment of the invention, the composite polypeptide is a single chain polypeptide, meaning that all amino acids are present in a single, peptide bonded polypeptide chain. This embodiment has the advantage that production of a desired single chain polypeptide product may be achieved very efficiently, since proper product conformation will depend on establishment of only the necessary secondary and tertiary polypeptide structures; quaternary polypeptide structure, in which separate polypeptides exhibiting a certain tertiary structure associate intermolecularly, need not be considered when the expressed composite polypeptide is a single chain composite polypeptide.

According to a further embodiment of the invention, the EED may be located at the C-terminal end or the N-terminal end of the composite polypeptide. Each location entails the intended advantages described hereinabove, especially the observed increase in total amount of expressed composite polypeptide. A C-terminally located EED will be expressed last, i.e. after the desired polypeptide, with the effect that any disulfide bonds necessary within the desired polypeptide will have time to form as necessary for protein stabilization prior to the translation of the EED. This means that when the EED is fully translated, the desired disulfide bond between Cys1 and Cys2 within the EED will be the last disulfide bond to form, and that the structure of the desired polypeptide will already have been stabilized by any internal disulfide bonds. The danger of the formation of undesired disulfide bonds between Cys1 or Cys2 in the EED portion of the composite polypeptide and another cysteine residue within the desired polypeptide is therefore minimal.

Positioning the EED at the N-terminal end of the composite polypeptide has the effect that the nucleic acid encoding the EED will be translated before the nucleic acid encoding the desired polypeptide. This means that a disulfide bond between Cys1 and Cys2 within the EED is likely to form before any other cysteine residue within the desired polypeptide is translated. Again here, the danger of an undesired disulfide bond forming between Cys1 or Cys2 in the EED portion of the composite polypeptide and a cysteine residue within the desired polypeptide is minimal.

Location of the EED at the N-terminal or C-terminal end of the composite polypeptide may therefore be determined by considerations of where the derivatization moieties to be bound to the EED would be least likely to perturb the biological activity of the desired polypeptide. In this way, a high degree of experimental flexibility is achieved; the experimenter has the luxury of choosing the location of the EED which will allow the highest activity of the desired polypeptide in the final derivatized composite polypeptide, without having to sacrifice the advantages conferred by the presence of the EED, these advantages having been explained above.

According to a preferred embodiment of the invention, the EED of the composite polypeptide is of the form: -Cys1-(Xaa)n-Cys2-(Pro)m, wherein n is any integer from 2 to 20; m is 0 (zero) or 1; and wherein Xaa is allowed at each position to be any of the naturally occurring amino acids, wherein preferably at least 75%, even better at least 80 or 90% of the Xaa residues are selected from Gly, Ala, Val, Leu, Ile, Ser, Thr, Met, Tyr, Asn, and Gln. In a preferred embodiment, all Xaa are Gly, Ser, Ala, or Thr. By allowing the variable n to range from 2, preferably 3, to 20, the linker between Cys1 and Cys2 remains short enough to promote formation of a disulfide bond between Cys1 and Cys2, yet long enough to allow the linker to double back on itself to do so. Linker lengths of 4-5 have been found to promote disulfide linkages between Cys1 and Cys2 especially efficiently, with a linker length of 4 amino acids being especially preferred for this purpose. Of the amino acids listed above in this paragraph, Gly and Ser, both alone and in mixtures, have been found to be especially amenable to this purpose. Without being bound by theory, the inventors believe this to be due to the fact that Gly is both chemically neutral and small, thereby reducing the propensity of the linker to participate in undesired chemical reactions while retaining a maximum degree of unhindered steric flexibility. The amino acid Ser is believed to confer, through its hydroxyl group, an adequate measure of hydrophilicity which may help in preventing a linker which is too hydrophobic from engaging in undesired hydrophobic interactions with hydrophobic regions of the desired polypeptide. It should be noted that in the event that the EED is located at the N-terminal end of the composite polypeptide, it may be advantageous that m is 0 (zero).

The present embodiment of the invention also allows a Pro residue to be peptide-bonded to Cys2 at the latter's C-end, although the presence of Pro is not a requirement (i.e. the variable m can also equal zero). The provision of Pro has been found to further increase expression yields of the composite polypeptide in some circumstances. Without being bound by theory, the inventors believe that this is due to proline's ability to inhibit proteinase degradation of the composite polypeptide from the latter's C-terminal end.

In an especially preferred embodiment of the invention, n=4 and (Xaa)4 (SEQ ID NO:1) is (Gly)4 (SEQ ID NO:2), (Gly)3Ser (SEQ ID NO:3), (Gly)2SerGly (SEQ ID NO:4), GlySer(Gly)2 (SEQ ID NO:5) or Gly(Ser)3 (SEQ ID NO:6). In another especially preferred embodiment of the invention, n=5 and (Xaa)5 (SEQ ID NO:7) is (Gly)5 (SEQ ID NO:8), (Gly)4Ser (SEQ ID NO:9), (Gly)3SerGly (SEQ ID NO:10), (Gly)2Ser(Gly)2 (SEQ ID NO:11), GlySer(Gly)3 (SEQ ID NO:12) or Ser(Gly)4 (SEQ ID NO:13). The special advantages of using Gly and Ser, both alone and together, in the linker of the EED have been discussed above. As mentioned above, a linker length of 4 amino acids in total was found to lead to the most efficient formation of a disulfide peptide loop between Cys1 and Cys2.

In a further embodiment of the invention, the EED is of the form (His)j-Cys1-(Xaa)n-Cys2-(Pro)m (SEQ ID NO:14) or Cys1-(Xaa)n-Cys2-(His)j-(Pro)m (SEQ ID NO:15) wherein j is any integer from 2 to 15, and wherein Xaa, n and m are as defined above. Incorporation into the EED of a poly-His sequence ("His-tag") to the N-side of Cys1 or to the C-side of Cys2 entails several advantages. First, as is known in the art (Porath, J., et al. (1975) Nature 258, 598-9; Sulkowski, E. (1985) Trends in Biotech 3, 1-12), a His-tag can be an invaluable tool in the isolation of expressed polypeptide via an immobilized nickel column as well as in the subsequent detection of the polypeptide. But perhaps more advantageous for the composite polypeptide of the present invention is the special effect that the His-tag has on the desired formation of the disulfide linkage between Cys1 and Cys2, and thus on the total amount of composite polypeptide obtained in expression. This effect is especially pronounced when the EED is located C-terminal to the desired polypeptide with the His-tag N-terminal of Cys1; or when the EED is located N-terminal to the desired polypeptide with the His-tag C-terminal of Cys2—in each case the His-tag is located at the interface of the EED and the desired polypeptide. Without being bound by theory, the inventors believe that this special effect may be explained as follows: Histidine typically bears a positive charge, so the individual histidine residues in a repeating histidine motif tend to be electrostatically repelled from one another, leading to an extended polypeptide chain in the region of the histidine residues. By placing this histidine motif within the EED at the interface between the desired polypeptide and the EED, these two components of the composite polypeptide become extended as far away from one another as the length of the His-tag allows. This has the effect of reducing the likelihood of unwanted interactions between the portion of the EED comprising Cys1 and Cys2 on the one hand, and the desired polypeptide on the other. At the same time, by physically separating the EED from the desired polypeptide, the likelihood that Cys1 and Cys2 will form a disulfide bond with one another is increased. This is because Cys1 and Cys2 exist in this scenario in more or less physical isolation from the rest of the nascent composite polypeptide; in the absence of any other sulfhydryl groups competing with Cys1 or Cys2 for formation of a disulfide bond, a disulfide bond is more likely to form in the desired fashion between the respective sulfhydryl groups on Cys1 and Cys2.

In an especially preferred embodiment of the invention, j=6, i.e. the EED is of the form (His)6-Cys1-(Xaa)n-Cys2-(Pro)m (SEQ ID NO:16) or Cys1-(Xaa)n-Cys2-(His)6-(Pro)m (SEQ ID NO:17), wherein Xaa, n and m are as defined above.

According to a further embodiment of the invention, the derivatized Cys1 and/or Cys2 is the reaction product of the Cys1 and/or Cys2 residue/s with a derivatization moiety comprising, e.g., a maleimide group, a sulfhydryl group, or a pyridyl disulfide group. All these chemical groups react covalently with sulfhydryl. The advantage of this embodiment of the present invention is that the majority of derivatization moieties which would be of interest for use in derivatizing the composite polypeptide are available in a form functionalized with one of the above groups. As such, the composite polypeptide of the invention can be derivatized with a wide variety of various reagents for various therapeutic and/or diagnostic purposes. Of the groups mentioned above, a maleimide group is especially preferred. The maleimide group reacts nearly completely with sulfhydryl under mild reaction conditions which would not likely damage the desired polypeptide in the composite polypeptide, and results in a robust covalent chemical bond between the sulphur atom of cysteine and one of the two unsaturated carbon atoms in the ring of the maleimide group.

In an especially preferred embodiment of the invention, the derivatization moiety comprising a maleimide group is chosen from PEG-maleimide ("PEG-MAL"), a maleimide-functionalized fluorescence marker, a maleimide-functionalized assay detection marker, a maleimide-functionalized radioactive tracer, a maleimide-functionalized protein crosslinker, a maleimide-functionalized chemotherapeutic agent or a maleimide-functionalized toxin, for example a maleimide-functionalized immunotoxin. Suitable examples of PEG-MAL are methoxy PEG-MAL 5 kD; methoxy PEG-MAL 20 kD; methoxy (PEG)2-MAL 40 kD; methoxy PEG(MAL)2 5 kD; methoxy PEG(MAL)2 20 kD; methoxy PEG(MAL)2 40 kD; or any combination thereof. Any of these reagents may be used as derivatization moieties to confer the known advantages of PEGylation, including increasing the serum half time and reducing the immunogenicity, of the composite polypeptide of the invention. Suitable examples of a maleimide-functionalized fluorescence marker are biotin-maleimide and digoxygenin-maleimide. A suitable example of a maleimide-functionalized radioactive tracer is DTPA-maleimide. A suitable example of a maleimide-functionalized crosslinker is an N-hydroxysuccinimidyl-maleimide crosslinking species which reacts through its N-hydroxysuccinimidyl portion with a free amino group of another chemical species to be coupled, and through its maleimide portion with at least one of Cys1 and Cys2 on the composite polypeptide of the invention. The crosslinking species may advantageously be used to effect, through its N-hydroxysuccinimidyl portion, e.g. a glycosylation, a silylation or a pectinylation of the composite polypeptide of the invention.

According to a further embodiment of the invention, Cys1 and/or Cys2 is derivatized with a derivatization moiety comprising a sulfhydryl group, in particular wherein said derivatization moiety is Cys2 coupled to Cys1 by a disulfide bond. The scenario in which Cys1 forms a disulfide bond with Cys2 is discussed above. A further example of a derivatization of Cys1 or Cys2 with a derivatization moiety comprising a sulfhydryl group is when the derivatization moiety is a polypeptide or protein other than the composite polypeptide of the invention, and the derivatization is accomplished by formation of a disulfide bond between, on one side, Cys1 and/or Cys2 of the composite polypeptide of the invention and, on the other side, with a Cys residue of the other polypeptide or protein. A further possibility of a derivatization moiety comprising a sulfhydryl group is a derivatization moiety comprising a 5-thio-2-nitrobenzoic acid ("TNB-thiol") group.

According to a further embodiment of the invention, both Cys1 and Cys2 are derivatized with derivatization moieties. This leads to two derivatization moieties per inventive composite polypeptide molecule. Such derivatization might be especially advantageous when derivatizing a composite polypeptide intended for use as an imaging reagent. This is because double-derivatization per composite polypeptide would lead to an imaging signal twice as intense as would result using a composite polypeptide derivatized with only one derivatization moiety per molecule. Double-derivatization per composite polypeptide is also envisioned as being advantageous under certain circumstances in which the composite polypeptide is intended for use as a therapeutic agent. For instance, if it is desired to PEGylate the composite polypeptide prior to therapeutic administration and a total molecular weight due to PEG of 40 kD is desired, it may prove more advantageous to derivatize the composite polypeptide at Cys1 and Cys2 with two respective molecules of 20 kD PEG-MAL than to derivatize only at Cys1 or Cys2 with one molecule of 40 kD PEG-MAL. Generally, derivatization at each of Cys1 and Cys2 can be accomplished by reacting the composite polypeptide of the invention with a molar excess of derivatization moiety.

According to a further embodiment, either Cys1 or Cys2 is derivatized with a first derivatization moiety, while the respective other of Cys2 and Cys1, respectively, is derivatized with a second derivatization moiety, wherein the second derivatization does not exhibit any functionality other than to block/protect the Cys residue to which it is bound. Conversely to the scenario described above, it may sometimes be advantageous or necessary to derivatize the composite polypeptide of the invention only once, for example, when using the composite polypeptide as a diagnostic reagent in a situation where a 1:1 correlation is needed between the biological activity of the desired polypeptide within the composite polypeptide and the signal measured. Similar scenarios can be envisioned in which, say, it would be desirable or necessary to PEGylate a composite polypeptide of the invention at only one position. In such cases, the composite polypeptide can be advantageously incubated under mild reducing conditions sufficient to reduce the disulfide bond existing between Cys1 and Cys2, but not any other disulfide linkages existing throughout the structure of the desired polypeptide to stabilize the latter's structure. Such selective reduction under mild conditions will typically be possible, since disulfide bonds involved in stabilization of polypeptide structure will normally be buried within this polypeptide structure and therefore poorly accessible by reduction agents in solution, whereas the more exposed, C-terminal EED will generally be more accessible. Following opening of the disulfide bond within the EED, the composite polypeptide of the invention can then be reacted with the desired first derivatization moiety such that the molar amount of first derivatization moiety is equal to or slightly less than the molar amount of inventive composite polypeptide. Precise stoichiometric adjustment of this ratio may be necessary depending on the first derivatization moiety used, but such adjustment lies well within the ambit of the skilled practitioner's expertise.

Following reaction of either Cys1 or Cys2 with the first derivatization moiety, the singly-derivatized composite polypeptide may be isolated by standard techniques and advantageously subjected to a further reaction with a second derivatization moiety. The function of the second derivatization moiety is to deactivate the remaining free sulfhydryl group of the underivatized cysteine residue within the EED. To ensure that the reaction with the second derivatization moiety is efficient, this reaction should advantageously be performed in a molar excess of second derivatization moiety to composite polypeptide. In this sense, a second derivatization moiety may be any moiety which will react covalently with the remaining free cysteine residue within the EED, and may employ any of the coupling chemistries mentioned above in the context of the first derivatization moiety. Since the function of the second derivatization moiety is merely to render the remaining cysteine residue within the EED permanently unreactive, the second derivatization moiety should not interfere with the intended activity of the desired polypeptide or the first derivatization moiety connected to the other cysteine residue in the EED. For this reason, the second derivatization moiety should be chemically and electrostatically inert and as small as possible. An especially preferred second derivatization moiety is ethyl-maleimide. This second derivatization moiety will react with the free sulfhydryl group of the remaining cysteine residue in the EED to form a covalent C-S bond in the matter already described above.

According to a further embodiment of the invention, the desired polypeptide may be any polypeptide for which adequate expression is desired. This includes all protein and polypeptide molecules of various sizes (i.e. molecular weights), irrespective of isoelectric points, primary amino acid sequence or desired posttranslational modifications such as for example glycosylation or phosphorylation. The desired polypeptide may advantageously be a receptor, a ligand or a binding molecule. It may be expressed in prokaryotes or in eukaryotes, and may itself be of natural or recombinant origin.

According to an especially preferred embodiment of the invention, the desired polypeptide has an even number of cysteine residues required for stabilization of polypeptide structure. This will normally be the case, especially when the desired polypeptide is a single chain polypeptide (i.e. will not interact with any other polypeptide chain following expression to form a multichain polypeptide product), since each disulfide bond required for stabilizing polypeptide structure requires that two cysteine residues be present.

According to an especially preferred embodiment of the invention, the desired polypeptide is a binding molecule in the form of an antibody. Encompassed within the meaning of "antibody" within this embodiment of the invention are single chain mono- and bispecific antibodies, as well as antibodies. comprising multiple polypeptide chains, such as immunoglobulin molecules (in which it may be advantageous to express each constituent polypeptide chain thereof with an EED of its own) or diabodies (in which two scFv molecules, each with an EED of its own, associate linearly head-to-tail to form a molecular species capable of binding two distinct antigens). Such immunoglobulin molecules may be either monospecific (i.e. each of the two binding arms of the immunoglobulin bind to the same antigen) or bispecific (i.e. each of the two binding arms of the immunoglobulin bind to different antigens), for example such bispecific immunoglobulins as would be obtained from a hybrid-hybridoma.

In an especially preferred embodiment of the invention, the desired polypeptide is a monospecific single chain antibody. Within the meaning of the present invention, the term "monospecific single chain antibody" may be understood as a single polypeptide chain comprising at least one antibody variable region. This at least one antibody variable region may be present in nature, for example in an antibody library of natural origin, or may be synthetic in that it comprises elements found in or derived from nature, but these elements are present in combinations not present as such in nature. Alternatively, a monospecific single chain antibody may comprise both natural and synthetic elements. Specifically falling within the meaning of the term "monospecific single chain antibody" are single domain antibodies, scFv molecules, as well as humanized and/or deimmunized variants thereof.

According to a further especially preferred embodiment of the invention, the desired polypeptide may be a bispecific single chain antibody. Within the meaning of the present invention, the term "bispecific single chain antibody" may be understood as two monospecific single chain antibodies as described above existing on a single polypeptide chain, and preferably separated from one another by a suitable polypeptide spacer sequence. Examples of such spacers may be found e.g. in EP 623679 B1 and U.S. Pat. No. 5,258,498. As such, the composite polypeptide may advantageously represent a derivatized bispecific antibody.

According to a further embodiment of the invention, the bispecific single chain antibody comprises a first monospecific single chain antibody (first binding portion) specifically binding to an effector antigen and a second monospecific single chain antibody (second binding portion) specifically binding to a target antigen. This general construction has the advantage that the desired polypeptide can specifically bind with its first binding portion to an effector antigen such that the effector antigen bound for example becomes activated. The biological activity triggered by this effector antigen may then be directed to, for example, a cell bearing the target antigen, to which the second portion of the bispecific single chain antibody specifically binds. Here, it is to be understood that the terms "first" and "second" imply no restriction with respect to the location of the antibody portions relative to the N-terminus or C-terminus of the polypeptide. It is therefore within the ambit of this embodiment of the invention that the composite polypeptide comprises a desired polypeptide in which the first binding portion specifically binding to the effector antigen may be located towards the desired polypeptide's N-terminal end or C-terminal end.

In an especially preferred embodiment of the invention, the effector antigen is chosen from the CD3 antigen, the CD64 antigen, the CD89 antigen and the NKG2D antigen. In another preferred embodiment of the invention, the target antigen is chosen from EpCAM, CCR5, CD19, HER-2 neu, HER-3, HER-4, EGFR, PSMA, CEA, MUC-1 (mucin), MUC2, MUC3, MUC4, MUC5AC, MUC5B, MUC7, hCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6; desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRvIII, LG, SAS and CD63. Here, all the above antigens (both effector and target antigens) may be human antigens.

In a very preferred embodiment of the invention, the target antigen is the human CD19 antigen, while the effector antigen is the human CD3 antigen. As such, this embodiment provides for a derivatized composite polypeptide capable of directing the cytotoxic potential of cytotoxic T cells against B lymphocytes bearing the CD19 antigen. Such a medication has great potential as a therapeutic agent in the treatment of B cell malignancies. As a result, it is of great interest to derivatize such a composite polypeptide in its EED with one or more PEG molecules in order to increase the serum half time while simultaneously reducing the immunogenicity of the composite polypeptide.

In another very preferred embodiment of the invention, the target antigen is the human EpCAM antigen, while the effector antigen is the human CD3 antigen. As such, this embodiment provides for a derivatized composite polypeptide capable of directing the cytotoxic potential of cytotoxic T cells against cells bearing the EpCAM antigen. The EpCAM antigen is expressed in many human malignant cells; such a derivatized composite polypeptide therefore has great potential in the treatment of a wide spectrum of human cancers. As with the anti-CD3xanti-CD19 composite polypeptide described above, it is also of great interest to derivatize such an anti-CD3xanti-EpCAM composite polypeptide in its EED with one or more PEG molecules.

A further aspect of the invention relates to a composition comprising any of the composite polypeptides described above and a pharmaceutically acceptable carrier.

In a further aspect, the invention provides a method of producing a composite polypeptide, wherein the composite polypeptide comprises a desired polypeptide and is expressed in higher yield than the desired polypeptide, said method comprising a) providing a nucleotide sequence encoding the desired polypeptide;
b) incorporating on either end of the nucleotide sequence encoding the desired polypeptide a nucleotide sequence encoding an expression enhancing domain ("EED") encoding, said nucleotide sequence encoding the EED comprising codons for first and second cysteine amino acid residues Cys1 and Cys2, respectively, the codon for Cys1 being located closer to the 5'-end of the nucleotide sequence than the codon for Cys2, wherein the codons for Cys1 and Cys2 are separated by a nucleotide sequence encoding a polypeptide linker, said linker being cysteine-free; and defining a length sufficient to allow Cys1 and Cys2 to engage in an intramolecular disulfide bond with one another;
c) transfecting the nucleotide sequence from step (b) into a host expression system in a suitable vector;
d) incubating the host expression system under conditions suitable to result in expression of the nucleotide sequence from step (b);
e) isolating the polypeptide expressed in step (d) to obtain the composite polypeptide.

A preferred embodiment of this aspect of the invention comprises the further step of derivatizing the composite polypeptide obtained in step (e) at Cys1 and/or Cys2. Such derivatization may be performed as described above, namely by reducing the intramolecular disulfide bond between Cys1 and Cys2 (this intramolecular disulfide bond itself being seen as a derivatization) under reducing conditions (for example using dithiothreitol, or DTT), followed by reaction of the reduced product with another derivatization moiety bearing a chemical group which reacts with at least one of the free thiol groups of Cys1 and Cys2.

The invention will now be described in more detail by way of the following nonlimiting figures and examples.

The invention will now be described in further detail by way of the following, non-limiting examples.

EXAMPLES

Example 1

Cloning and Expression of scFv with a C-terminal (His)6-Cys-(Gly)4-Cys-Pro (SEQ ID NO:20) tag (i.e. scFv with an EED as defined above)

An scFv molecule, i.e. a polypeptide unifying heavy and light chain antibody variable regions and a (Gly4Ser)3 (SEQ ID NO:30) polypeptide linker disposed therebetween, was used as a model molecule for demonstrating the concept of the invention. This scFv specifically binds to a predetermined antigen, subsequently referred to as "Antigen". An scFv with a C-terminal (His)6-Cys-(Gly)4-Cys-Pro (SEQ ID NO:20) tag was constructed by a PCR-reaction with VL-specific primers, whereas the scFv nucleotide sequence was independently extended with each of the respective nucleotide sequences of the (His)6-Cys-(Gly)x-Cys-Pro motif (A: TGCGGTGGCTGCCCGTAA (SEQ ID NO:21), B: GCGGTGGCGGTTGCCCGTAA (SEQ ID NO:22), C: TGCGGTGGCGGTGGCTGCCCGTAA (SEQ ID NO:23), D: TGCGGTGGCGGTGGCGGTGGCTGCCCGTAA) (SEQ ID NO:24). This yielded four nucleotide sequences encoding 4 separate scFvs, each with a C-terminal tag having two cysteine residues separated by glycine linkers of varying length. The His-Tag was employed in later detection and purification steps. The resulting VL fragments were subcloned via the restriction enzyme recognition sites SalI and NotI (introduced by PCR) into pBADpelB (derived from the vector pBADMycA-His from Invitrogen) containing the corresponding VH behind a pelB leader sequence for periplasmic expression. After transformation into heat shock competent *E.coli* XL1Blue, a single clone was cultivated in selective media (LB 50µg/ml Carbenicillin) and the plasmid was prepared according to standard protocols. Successful cloning was confirmed by sequencing the insert (Sequiserve, Munich).

*E.coli* BL21DE3 were transformed with the expression plasmid coding for the respective scFv with one or two C-terminal Cys residues and grown on selective agar. One colony was used to inoculate 5 ml LB 50 g/ml Carbenicillin over night at 37° C. For the production culture, 500 ml SB growth medium containing 20 mM MgC12 and 50 µg/ml Carbenicillin in 2 l shaker flasks were inoculated with the bacterial suspension of the overnight culture and further incubated at 37° C. to an optical density at OD600 of 0.6-0.8. Protein production was induced by adding L-arabinose to a final concentration of 0.2% and reduction of the temperature to 30° C. After a four hour production phase at 30° C. the bacteria were harvested and resuspended in 40 ml PBS. Through four rounds of freezing at −70° C. and thawing at 37° C. the outer membrane was destroyed by temperature shock and the soluble periplasmic proteins including the scFv-fragments were released into the liquid. After elimination of intact cells and cell debris by centrifugation, the supernatant was used for ELISA analysis.

Figure 1:
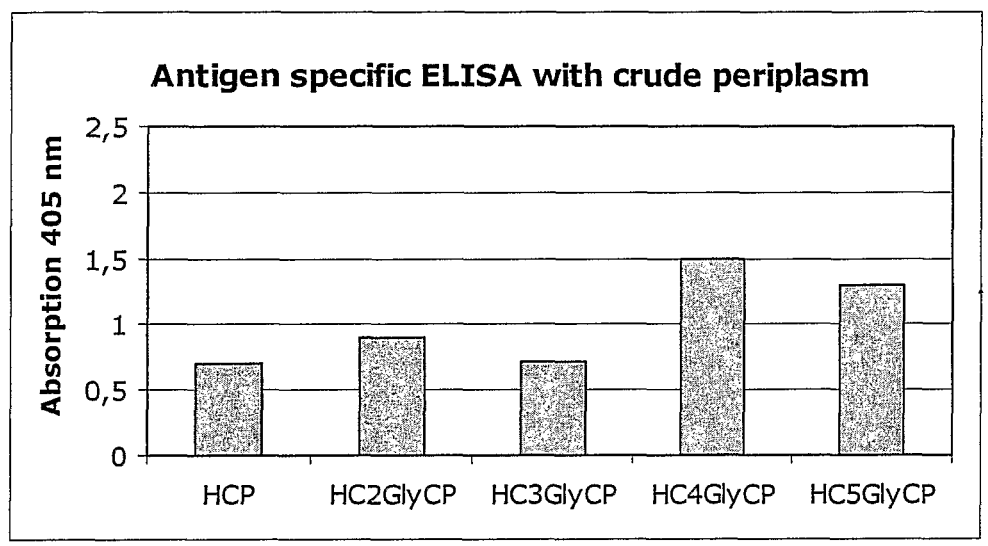
FIG. 1 Antigen-specific ELISA as dependent on linker length between Cys1 and Cys2

ELISA analysis of the periplasmic preparation was carried out using an ELISA-plate (Nunc MaxiSorp) coated with ProteinL (2µg/ml in PBS). Coating was performed overnight at 4° C. After washing with PBS 0.05% Tween, the plate was blocked with 100 µl PBS containing 3% BSA for 1h at room temperature. After washing, 50 µl periplasm were added, diluted serially 1:3 and incubated for 1 h at room temperature. After an additional washing step, detection of scFv bound to ProteinL was carried out specifically using 50 µl Antigen-Biotin (1.5 µg/ml containing PBS 1% BSA) detected by streptavidin-HRP (Dako, 1 µg/ml in PBS containing 1% BSA). The signal was detected by adding 100 µl ABTS (2,2'-Azino-di[3-ethylbenzthiazoline sulfonate (6)] diammonium salt)-substrate solution for 15-30 min. The OD-values were measured on an ELISA reader at a wavelength of 405 nm. The results are shown in FIG. 1, in which "HCP", CH2GlyCP", "HC3GlyCP", "HC4GlyCP" and "HC5GlyCP" respectively refer to scFv molecules with C-terminal tags containing (His) 6-Cys-Pro (SEQ ID NO:19), (His)6-Cys-(Gly)2-Cys-Pro (SEQ ID NO:25), (His)6-Cys-(Gly)3-Cys-Pro (SEQ ID NO:26), (His)6-Cys-(Gly)4-Cys-Pro (SEQ ID NO:20) and (His)6-Cys-(Gly)5-Cys-Pro (SEQ ID NO:27). As can be seen in FIG. 1, the highest yield of scFv binding to Antigen was observed for the construct with four glycines used as linker between the two C-terminal cysteines.

Example 2

Confirmation of the Higher Protein Yield of scFv with (His)6-Cys-(Gly)4-Cys-Pro (SEQ ID NO:20) tag (i.e. an EED, as defined above) as compared to the scFv with (His)6-Cys-Pro (SEQ ID NO:19) tag (i.e. without an EED as defined above).

Figure 2:
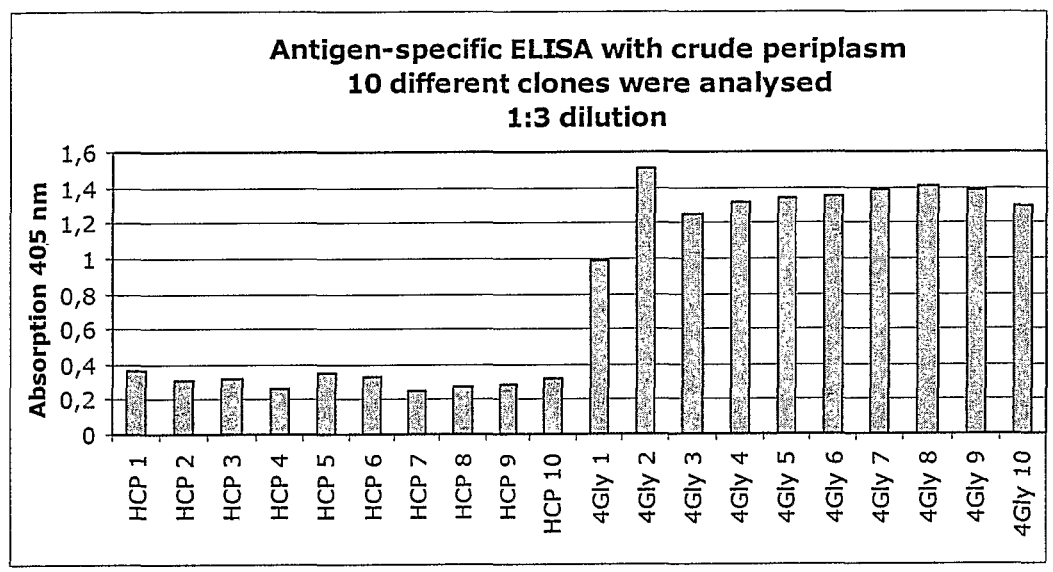
FIG. 2 Antigen-specific ELISA results as a measure of expression yields with one C-terminal cysteine residue, and with two C-terminal cysteine residues separated by a 4-glycine linker FIG. 3 Western blot results as a measure of expression yields with one C-terminal cysteine residue, and with two C-terminal cysteine residues separated by a 4-glycine linker (1. and 2. (SEQ ID NO:18); 3. and 4. (SEQ ID NO:19); 5. and 6. (SEQ ID NO:20)

Protein expression levels of the scFv extended with (His) 6-Cys-(Gly)4-Cys-Pro (SEQ ID NO:20) tag (i.e. seFv with the EED as defined above, referred to as "4Gly" in FIG.2) and the scFv extended with the (His)6-Cys-Pro (SEQ ID NO:19) C-terminal tag (i.e. scFv without the EED as defined above, referred to as "HCP" in FIG.2) were compared. Both constructs were analyzed on small scale using the *E.coli* strain BL21DE3. In each case 10 different colonies were inoculated in 5 ml SB/20mM MgCl2/50 µg/ml Carbenicillin for four hours at 37° C. in a shaking incubator. Again protein production was initiated by the addition of 0.2% L-arabinose to the cell cultures and a temperature decrease to 30° C. After an overnight induction period cells were harvested, resuspended in 1 ml PBS and the periplasmic fraction was isolated by the freeze/thaw method and analyzed in an Antigen-specific ELISA as described in Example 1. The results of this analysis are shown in FIG. 2. The ELISA results show clearly the significantly increased yield of scFv with the (His)6-Cys-(Gly)4-Cys-Pro (SEQ ID NO:20) tag ("4Gly") in the crude periplasm as compared to the scFv species containing a C-terminal (His)6-Cys-Pro (SEQ ID NO:19) motif, but lacking a second cysteine residue. Clearly, then, the ability to form a controlled, intramolecular disulfide bond between the two cysteine residues in the C-terminal tag (i.e. the EED as defined above) is of crucial importance for achieving the enhanced production yields observed.

The periplasmic fractions were further analyzed by non-reducing SDS-PAGE followed by Western blot techniques according to standard protocols. The detection of the His-tagged scFv was accomplished using an anti-penta His antibody, Qiagen (1 µg/ml in PBS containing 0.1% BSA) detected with an alkaline phosphatase-conjugated goat anti-mouse antibody, Sigma (1 µg/ml in PBS containing 0.1% BSA). The protein blot was developed by adding BCIP/NBT substrate solution (Sigma, B-1911). The results are shown in FIG. 3.

Figure 3:
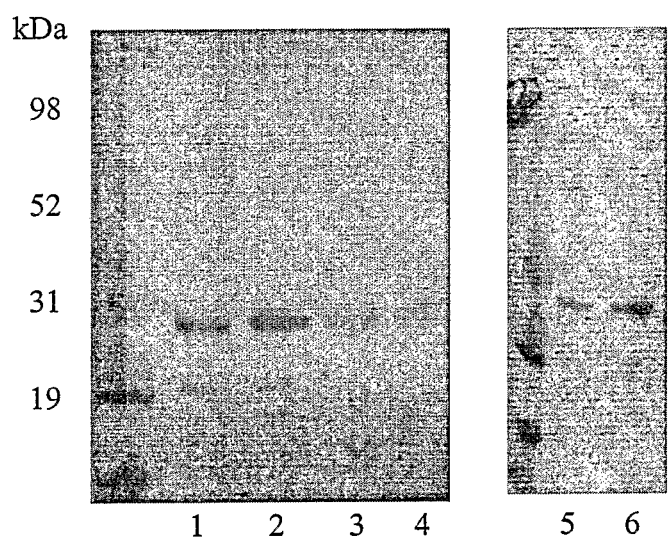

Lanes 1 and 2 of the Western blot shown in FIG. 3 show bands of scFv with (His)6-Pro (SEQ ID NO:28) at the C-terminal end. The intensity of scFv bands in the Western blot—and therefore the amount of total polypeptide expressed—is seen to decrease drastically in lanes 3 and 4, corresponding to scFv with (His)6-Cys-Pro (SEQ ID NO:19) at the C-terminal end of the polypeptide. Lanes 5 and 6, corresponding to scFv with (His)6-Cys-(Gly)4-Cys-Pro (SEQ ID NO:20) at the C-terminal end of the polypeptide, show a band intensity which is once again comparable to the intensity seen in lanes 1 and 2. This clearly demonstrates that the loss in protein expression suffered in adding a single cysteine residue to the C-terminal end of the scFv polypeptide (lanes 3 and 4) was regained by adding a second cysteine residue, separated from the first cysteine residue by a polypeptide linker allowing disulfide bond formation between the two cysteine residues (lanes 5 and 6).

Taken together, the results of the ELISA (FIG. 2) and the Western blot (FIG. 3) analyses show clearly the higher protein/scFv yield of the scFv construct with two C-terminal cysteine residues as compared to the scFv construct with only one C-terminal cysteine.

Example 3

Purification of scFv with the (His)6-Cys-(Gly)4-Cys-Pro (SEQ ID NO:20) tag (i.e. the EED, as defined above)

E. coli BL21DE3 were transformed with the expression plasmid and grown on selective agar. A single colony was used to inoculate 5 ml LB 50 µg/ml Carbenicillin overnight at 37° C. For the production culture, 500 ml SB/20 mM MgC12/50 µg/ml Carbenicillin in 2 1 shaker flasks were inoculated with the bacterial suspension of the overnight culture and grown at 37° C. to an optical density at OD600 of 0.6-0.8. Protein production was induced by adding L-arabinose to a final concentration of 0.2% and reduction of the temperature to 30° C. After an overnight production phase at 30° C. the bacteria were harvested and resuspended in 40 ml PBS. The outer membrane was destroyed by temperature shock and the soluble periplasmic proteins including the scFv-fragment were released into the liquid. After elimination of intact cells and cell debris by centrifugation, the supernatant was further purified.

SCA molecules were initially purified by an IMAC affinity column interacting with the C-terminal His-Tag. This was performed using a Qiagen Ni-NTA superflow column according to the protocol provided by the manufacturer. The column was equilibrated with 20 mM sodium phosphate 0.4 M NaCl, pH 7.2 and the periplasmic preparation (40 ml) was applied to the column at a flow rate of 2 ml/min. Afterwards the column was washed with 5 column volumes of equilibration buffer containing 0.025 M imidazole to remove unbound sample. Elution was carried out using equilibration buffer containing 0.5 M imidazole in 5 column volumes. Eluted protein fractions were pooled for further purification steps.

Figure 4:
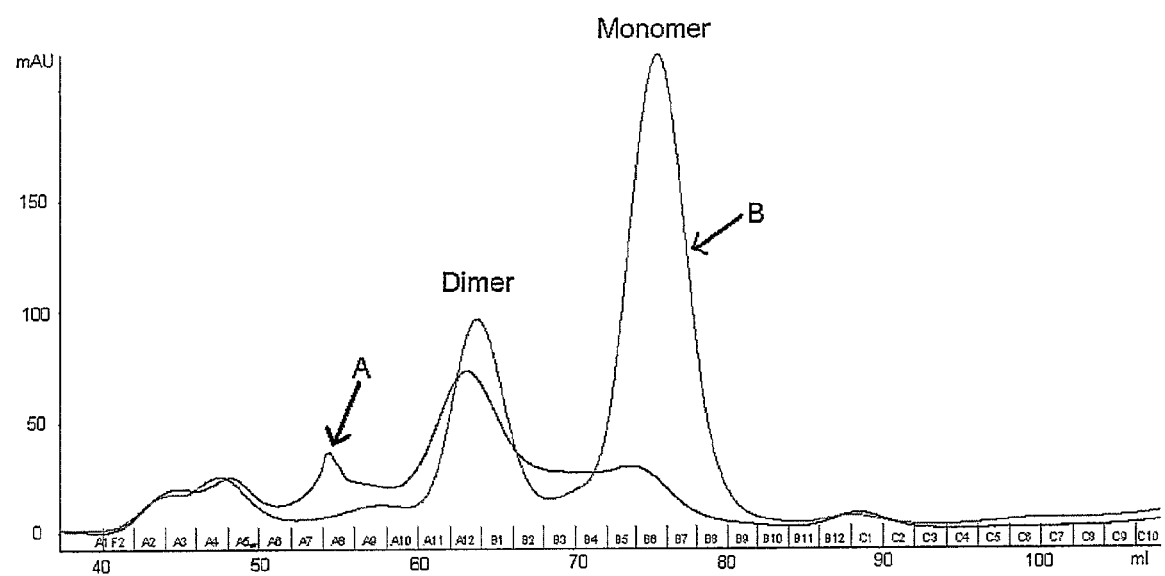
FIG. 4 Gel-filtration chromatography results showing an elution profile from a composite polypeptide according to the invention and an elution profile from a polypeptide with only one C-terminal cysteine residue FIG. 5 SDS-PAGE of the monomer and dimer scFv species obtained by gel-filtration chromatography; Gel results under non-reducing (left) and reducing (right) conditions are shown (1. and 2. (SEQ ID NO:19); 3. and 4. (SEQ ID NO:20)

To achieve a separation of the molecular weight, i.e. separation into multimeric, dimeric and monomeric fractions, gel filtration chromatography was performed on a superdex S75 prep grade column equilibrated with PBS (Gibco). Eluted protein monitored by continuous measurement of 280 nm light absorption (flow rate 1 ml/min) were subjected to standard SDS-PAGE. The results are shown in FIG. 4. FIG. 4 shows two elution profiles A and B, the lower one (profile A) being the elution profile of scFv with a C-terminal (His)6-Cys-Pro (SEQ ID NO:19) motif, the higher one (profile B) being the elution profile of scFv with a C-terminal (His)6-Cys-(Gly)4-Cys-Pro (SEQ ID NO:20) motif (i.e. scFv with the EED as defined above). As can clearly be seen, incorporation of a second cysteine residue in the C-terminal portion of the scFv in adequate separation from the first cysteine residue for the formation of a disulfide loop leads not only to a higher monomer:dimer product ratio, but also to a higher overall protein yield irrespective of monomer or dimer isoform.

This obvious optical analysis is corroborated by calculation of the isoform concentrations. The protein concentrations were calculated using the AUC value (determined by the UNICORN software) and the sequence-specific extinction coefficient. The concentration values obtained are summarized below in Table 1:

TABLE 1

| Amino Acid Sequence of C-terminal portion | Polypeptide isoform | Calculated concentration (µg/ml) | Sample volume (ml) | Total protein per isoform (µg) | Total protein (µg) |
| --- | --- | --- | --- | --- | --- |
| HHHHHHCP (SEQ ID NO: 19) | Monomer | 14.2 | 6 | 85.2 | 276.6 |
| HHHHHHGP (SEQ ID NO: 19) | Dimer | 31.9 | 6 | 191.4 | |
| HHHHHHCGGGGCP (SEQ ID NO: 20) | Monomer | 69 | 8 | 552 | 775.2 |
| HHHHHHCGGGGCP (SEQ ID NO: 20) | Dimer | 27.9 | 8 | 223.2 | |

From the above table, the following statements can be made. First, the monomer:dimer ratio for scFv with a single cysteine residue in its C-terminal portion is about 1:2.25. By addition of a second cysteine to the C-terminal portion of the scFv and by disposing a suitable linker between the first and second cysteine residues, an intramolecular disulfide bond is promoted, and the monomer:dimer ratio of obtained scFv is increased about 5.5 fold, to 1:0.4. Viewed from the standpoint of overall polypeptide yield irrespective of polypeptide isoform, the increase in yield from 276.6 µg for the scFv with a single cysteine residue to 775.2 µg for the scFv with two cysteine residues represents an increase in overall protein expression of about 280%, or almost 3-fold.

Figure 5:
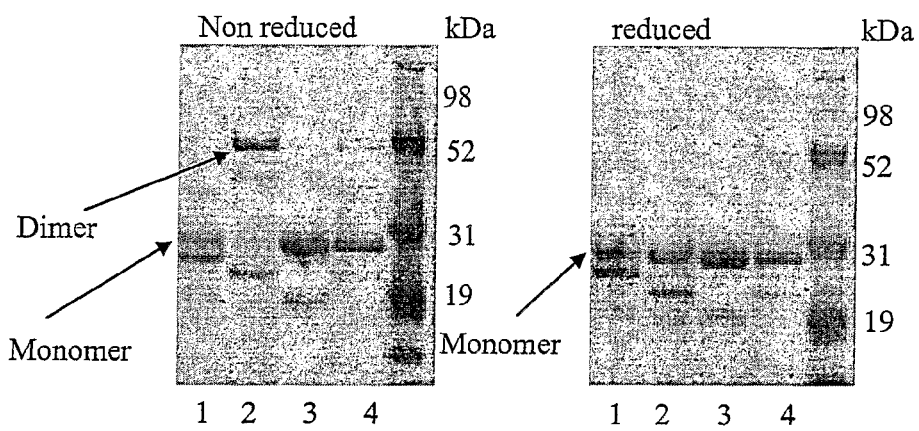

Analysis of the gel-filtered monomeric and dimeric fraction by SDS-PAGE under non-reducing and reducing conditions (FIG. 5) showed clearly that approximately 80% of the dimeric fraction of the scFv with a single cysteine in its C-terminal portion are dimeric, crosslinked by disulfide linkage (FIG. 5, non-reducing gel, lane 2), whereas the dimeric fraction of the scFv with two cysteine residues in its C-terminal portion exists mainly as a monomer, due to the formation of a disulfide loop between the two C-terminal cysteine residues (FIG. 5, non-reducing gel, lane 4). The dimer disaggregation into monomer (FIG. 5, non-reducing gel, lane 4) is an indication that aggregation had occurred only by protein-protein interaction and was not due to disulfide crosslinking. Lanes 1 and 3 of FIG. 5 (reducing and non-reducing conditions) show the corresponding monomer fractions.

The same samples were also run on a reducing gel (FIG. 5). Regarding the scFv without the (His)6-Cys-(Gly)4-Cys-Pro (SEQ ID NO:20) tag, lanes 2 shows that any dimer present in the non-reducing gel was in fact due to the formation of unwanted disulfide linkages between cysteine residues in two respective polypeptide molecules. The same holds true for the residual minimal amount of dimer of the scFv with the (His)6-Cys-(Gly)4-Cys-Pro (SEQ ID NO:20) tag (lane 4). The reducing conditions within the reducing gel suffice to open these disulfide linkages so that the only bands observed are the monomeric species of the scFv polypeptide in which no cysteine residue within the scFvs are able to form disulfide linkages with any other cysteine residue.

Example 4

Side directed PEGylation of scFvs with and without the C-Terminal (His)6-Cys-(Gly)4-Cys-Pro (SEQ ID NO:20) tag PEGylation at free cysteines should result in a stable homogeneous scFv-PEG conjugate. Two protein solutions containing, respectively, purified scFv with the C-terminal (His)6-Cys-(Gly)4-Cys-Pro tag and scFv with the C-terminal (His)6-Cys-Pro (SEQ ID NO:19) tag were incubated with DTT at a final concentration of 2 mM for one hour at room temperature to reduce the terminal disulfide bridge, resulting in two free sulfhydryl groups.

Gel filtration (Sephadex G25 M, Amersham) of each polypeptide separately to remove residual DTT was then performed using PBS as a running buffer. mPEG-Maleimide MW 20 kD (Shearwater, 2D2M0P01) was added to the first half of each polypeptide sample in a 10-fold molar excess of PEG molecules. The term "mPEG" here carries the known meaning, namely "methoxy polyethylene glycol". The other half of each polypeptide sample was incubated with a 10-fold molar excess of ethylmaleimide (Sigma, E-1271) as a control.

Each reaction was allowed to occur for 2 hours with agitation at room temperature. All samples were analyzed by SDS-PAGE under non-reducing conditions and stained with silver according to standard protocols (Invitrogen, Cat. No. LC6100). The results are shown in FIG. 6.

Figure 6:
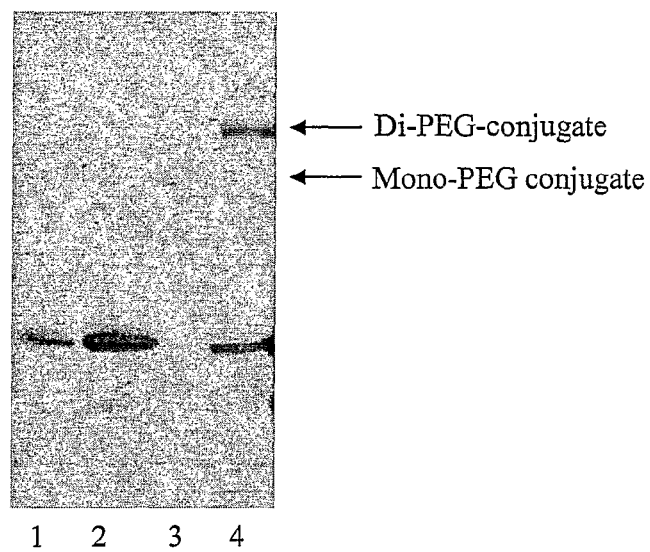
FIG. 6 SDS-PAGE of scFv with one and two C-terminal cysteine residues, before and after reaction with 20 kD PEG-maleimide (1. and 3. (SEQ ID NO:19); 2. and 4. (SEQ ID NO:20).

Lane 1 of FIG. 6 depicts scFv with (His)6-Cys-Pro (SEQ ID NO:19) at its C-terminal end. The cysteine residue has been blocked by reaction with ethylmaleimide. Lane 2 of FIG. 6 shows an scFv with (His)6-Cys-(Gly)4-Cys-Pro (SEQ ID NO:20) at its C-terminal end, in which both cysteine residues have been blocked by reaction with ethylmaleimide. The relative intensities of the bands in lanes 1 and 2 (i.e. the band in lane 2 is much more intense than the band at the same position in lane 1) is a measure of the enhanced expression efficiency achieved when expressing the scFv with two C-terminal cysteine residues as compared to that achieved when expressing the scFv with a single C-terminal cysteine residue.

Lane 3 of FIG. 6 shows the result of coupling an scFv with a single C-terminal cysteine residue with PEG-maleimide of 20 kD molecular weight. As can be seen in the upper portion of lane 3, only a very faint band of PEG-coupled scFv was obtained, the faintness of which is likely an indication of the poor expression yields, and therefore less absolute amounts of scFv obtained using scFv with only a single C-terminal cysteine residue. In sharp contrast, lane 4 of FIG. 6, in which the scFv with two C-terminal cysteine residues separated from one another by a 4-glycine linker has been reacted with 20 kD PEG, shows two distinct bands. One band is at the same molecular weight as the corresponding unreacted species, indicating that the reaction with 20 kD PEG did not proceed to completion. The other, higher band at heavier molecular weight is an indication that 20 kD PEG has reacted with both of the two cysteine residues in the C-terminal portion of the scFv, as it is of higher molecular weight than the PEGylation product of the scFv with only a single C-terminal cysteine residue. It should be emphasized that it was only possible to obtain sufficient cysteine-containing starting material for the subsequent PEGylation reaction by incorporating not one, but two cysteine residues in the C-terminal portion of the scFv, separated from one another by a 4-glycine linker.

The invention claimed is:

1. A composite polypeptide, said composite polypeptide comprising a desired polypeptide and an expression enhancing domain ("EED"), located at the C- or N-terminal end of the composite polypeptide, said EED comprising first and second cysteine amino acid residues Cys1 and Cys2, respectively, Cys1 being located closer to the N-terminus of the composite polypeptide molecule than Cys2, wherein Cys1 and Cys2 are separated by a polypeptide linker, said linker:
   being free of cysteine and proline;
   defining a length sufficient to allow Cys1 and Cys2 to engage in an intramolecular disulfide bond with one another; and
   having a flexible polypeptide conformation essentially free of secondary polypeptide structure in aqueous solution,
   wherein at least one of Cys1 and Cys2 is derivatized with a derivatization moiety, and wherein the desired polypeptide is an antibody.

2. The composite polypeptide of claim 1, wherein at least 75% of the amino acid residues in the linker are selected from Gly, Ala, Val, Leu, Ile, Ser, Thr, Met, Tyr, Asn, and Gln.

3. The composite polypeptide of claim 1 or 2, wherein the composite polypeptide is a single chain polypeptide.

4. The composite polypeptide of claim 1, wherein the EED is of the form:
   -Cys1-(Xaa)n-Cys2-(Pro)m (SEQ ID NO:29),
   wherein
   n is any integer from 2 to 20;
   m is 0 (Zero) or 1; and
   Xaa is allowed at each position to be Gly, Ala, Thr, or Ser.

5. The composite polypeptide of claim 4, wherein n=4 and (Xaa)4 (SEQ ID NO:1) is (Gly)4 (SEQ ID NO:2), (Gly)3Ser (SEQ ID NO:3), (Gly)2SerGly (SEQ ID NO:4), GlySer(Gly)2 (SEQ ID NO:5) or Gly(Ser)3 (SEQ ID NO:6).

6. The composite polypeptide of claim 4, wherein n=5 and (Xaa)5 (SEQ ID NO:7) is (Gly)5 (SEQ ID NO:8), (Gly)4Ser (SEQ ID NO:9), (Gly)3SerGly (SEQ ID NO:10), (Gly)2Ser (Gly)2 (SEQ ID NO:11), GlySer(Gly)3 (SEQ ID NO:12) or Ser(Gly)4_(SEQ ID NO: 13).

7. The composite polypeptide of claim 4, wherein the EED is of the form:
   -His-His-His-His-His-His-Cys1-(Xaa)n-Cys2-(Pro)m (SEQ ID NO: 16); or
   -Cys1-(Xaa)n-Cys2-His-His-His-His-His-His-(Pro)m (SEQ ID NO: 17).

8. The composite polypeptide of claim 1, wherein the derivatized Cys1 and/or Cys2 is the reaction product of the Cys1 and/or Cys2 residue/s with a derivatization moiety comprising a maleimide group, a sulfhydryl group or a pyridyl disulfide group.

9. The composite polypeptide of claim 8, wherein the derivatization moiety comprising a maleimide group is selected from PEG-maleimide ("PEG-MAL"), a maleimide-functionalized fluorescence marker, a maleimide-functionalized assay detection marker, a maleimide-functionalized radioactive tracer or a maleimide-functionalized protein crosslinker.

10. The composite polypeptide of claim 9, wherein the PEG-MAL is chosen from:
methoxy PEG-MAL 5 kD;
methoxy PEG-MAL 20 kD
methoxy (PEG)2-MAL 40 kD;
methoxy PEG(MAL)2 5 kD;
methoxy PEG(MAL)2 20 kD;
methoxy PEG(MAL)2 40 kD; or
any combination thereof.

11. The composite polypeptide of claim 8, wherein Cys1 or Cys2 is derivatized with a derivatization moiety comprising a 5-thio-2-nitrobenzoic acid ("TNB-thiol") group or a sulfhydryl group.

12. The composite polypeptide of claim 1, wherein both Cys1 and Cys2 are derivatized with derivatization moieties.

13. The composite polypeptide of claim 1, wherein either Cys1 or Cys2 is derivatized with a first derivatization moiety, while the respective other of Cys2 or Cys1, respectively, is derivatized with a second derivatization moiety.

14. The composite polypeptide of claim 13, wherein the second derivatization moiety is ethyl maleimide.

15. The composite polypeptide of claim 1, wherein the antibody is selected from a monospecific single chain antibody or a bispecific single chain antibody.

16. The composite polypeptide of claim 15, wherein the bispecific single chain antibody comprises a first portion specifically binding to an effector antigen and a second portion specifically binding to a target antigen.

17. The composite polypeptide of claim 16, wherein the effector antigen is selected from the human CD3 antigen, the human CD64 antigen, the human CD89 antigen and the human NKGZD antigen.

18. The composite polypeptide of claim 16 or 17, wherein the target antigen is selected from the group consisting of EpCAM, CCR5, CD19, HER-2 neu, HER-3, HER-4, EGFR, PSMA, CEA, MUC-1 (mucin), MUC2, MUC3, MUC4, MUC5AC, MUC5B, MUC7, hCG, Lewis-Y, CD20, CD33, CD30, ganglioside GD3, 9—O—Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNE-alpha precursor, STEAP, mesothelin, A33 Antigen, Prostate Stem Cell Antigen (PSCA), Ly-6; desmoglein 4, E- cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGERvIII, LG, SAS and CD63, and wherein all said antigens are human antigens.

19. A composition comprising the composite polypeptide of claim 1 and a pharmaceutically acceptable carrier.

20. The composite polypeptide of claim 1 wherein said derivization moiety is Cys2 coupled to Cys1 by a disulfide bond.

21. A method of producing a composite polypeptide wherein the composite polypeptide comprises a desired polypeptide and an expression enhancing domain ("EED") located at the C- or N-terminus of the composite polypeptide. said EED comprising first and second cysteine amino acid residues Cys1 and Cys2, respectively, Cys1 being located closer to the N-terminus of the composite polypeptide molecule than Cys2, wherein Cys1 and Cys2 are separated by a polypeptide linker, said linker:
being free of cysteine and proline;
defining a length sufficient to allow Cys1 and Cys2 to engage in an intramolecular disulfide bond with one another; and
having a flexible polypeptide conformation essentially free of secondary polypeptide structure in aqueous solution,
wherein at least one of Cys1 and Cys2 is derivatized with a derivatization moiety, and wherein the desired polypeptide is an antibody, and
wherein the composite polypeptide comprising the desired polypeptide is expressed in higher yield than the desired polypeptide, said method comprising;
a) providing a nucleotide sequence encoding the desired polypeptide;
b) incorporating on either end of the nucleotide sequence encoding the desired polypeptide a nucleotide sequence encoding an expression enhancing domain ("EED") encoding, said nucleotide sequence encoding the EED comprising codons for first and second cysteine amino acid residues Cys1 and Cys2, respectively, the codon for Cys1 being located closer to the 5'-end of the nucleotide sequence than the codon for Cys2, wherein the codons for Cys1 and Cys2 are separated by a nucleotide sequence encoding a polypeptide linker, said linker being cysteine-free; and defining a length sufficient to allow Cys1 and Cys2 to engage in an intramolecular disulfide bond with one another;
c) transfecting the nucleotide sequence from step (b) into a host expression system in a suitable vector;
d) incubating the host expression system under conditions suitable to result in expression of the nucleotide sequence from step (b); and
e) isolating the polypeptide expressed in step (d) to obtain the composite polypeptide.

22. The method of claim 21, further comprising the step of derivatizing the composite polypeptide obtained in step (e) at Cys1 and/or Cys2.

* * * * *

UNITED STATES PATENT AND TRADEMARK OFFICE
CERTIFICATE OF CORRECTION

PATENT NO. : 8,518,403 B2 Page 1 of 1
APPLICATION NO. : 11/572116
DATED : August 27, 2013
INVENTOR(S) : Hoffmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1960 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 30

<210> SEQ ID NO 1
<211> LENGTH: 4
<212> TYPE: PRT
<213> ORGANISM: Artificial Sequence
<220> FEATURE:
<223> OTHER INFORMATION: Linker sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 1

Xaa Xaa Xaa Xaa
1

<210> SEQ ID NO 2
<211> LENGTH: 4
<212> TYPE: PRT
<213> ORGANISM: Artificial Sequence
<220> FEATURE:
```

<223> OTHER INFORMATION: Linker sequence

<400> SEQUENCE: 2

Gly Gly Gly Gly
1

<210> SEQ ID NO 3
<211> LENGTH: 4
<212> TYPE: PRT
<213> ORGANISM: Artificial Sequence
<220> FEATURE:
<223> OTHER INFORMATION: Linker sequence

<400> SEQUENCE: 3

Gly Gly Gly Ser
1

<210> SEQ ID NO 4
<211> LENGTH: 4
<212> TYPE: PRT
<213> ORGANISM: Artificial Sequence
<220> FEATURE:
<223> OTHER INFORMATION: Linker sequence

<400> SEQUENCE: 4

Gly Gly Ser Gly
1

<210> SEQ ID NO 5
<211> LENGTH: 4
<212> TYPE: PRT
<213> ORGANISM: Artificial Sequence
<220> FEATURE:
<223> OTHER INFORMATION: Linker sequence

<400> SEQUENCE: 5

Gly Ser Gly Gly
1

<210> SEQ ID NO 6
<211> LENGTH: 4
<212> TYPE: PRT
<213> ORGANISM: Artificial Sequence
<220> FEATURE:
<223> OTHER INFORMATION: Linker sequence

<400> SEQUENCE: 6

Gly Ser Ser Ser
1

<210> SEQ ID NO 7
<211> LENGTH: 5
<212> TYPE: PRT
<213> ORGANISM: Artificial Sequence
<220> FEATURE:
<223> OTHER INFORMATION: Linker sequence
<220> FEATURE:
<221> NAME/KEY: misc_feature
<222> LOCATION: (1)..(5)
<223> OTHER INFORMATION: Xaa can be any naturally occurring amino acid

<400> SEQUENCE: 7

Xaa Xaa Xaa Xaa Xaa
1               5

<210> SEQ ID NO 8
<211> LENGTH: 5
<212> TYPE: PRT

```
<213> ORGANISM: Artificial Sequence
<220> FEATURE:
<223> OTHER INFORMATION: Linker sequence

<400> SEQUENCE: 8

Gly Gly Gly Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Linker sequence

<400> SEQUENCE: 9

Gly Gly Gly Gly Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Linker sequence

<400> SEQUENCE: 10

Gly Gly Gly Ser Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Linker sequence

<400> SEQUENCE: 11

Gly Gly Ser Gly Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Linker sequence

<400> SEQUENCE: 12

Gly Ser Gly Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Linker sequence

<400> SEQUENCE: 13

Ser Gly Gly Gly Gly
1               5

<210> SEQ ID NO 14
<211> LENGTH: 38
<212> TYPE: PRT
<213> ORGANISM: Artificial Sequence
<220> FEATURE:
```

```
<223> OTHER INFORMATION: Linker sequence
<220> FEATURE:
<221> NAME/KEY: MISC_FEATURE
<222> LOCATION: (1)..(15)
<223> OTHER INFORMATION: His at position 1-15 and up to 13 may be absent
<220> FEATURE:
<221> NAME/KEY: MISC_FEATURE
<222> LOCATION: (17)..(36)
<223> OTHER INFORMATION: Xaa at position 17-36 can be any natural
      occurring amino acid and up to 18 may be absent
<220> FEATURE:
<221> NAME/KEY: MISC_FEATURE
<222> LOCATION: (38)..(38)
<223> OTHER INFORMATION: Pro is optional

<400> SEQUENCE: 14

His His His His His His His His His His His His His His His Cys
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Cys Pro
        35

<210> SEQ ID NO 15
<211> LENGTH: 38
<212> TYPE: PRT
<213> ORGANISM: Artificial Sequence
<220> FEATURE:
<223> OTHER INFORMATION: Linker sequence
<220> FEATURE:
<221> NAME/KEY: MISC_FEATURE
<222> LOCATION: (2)..(21)
<223> OTHER INFORMATION: Xaa at position 2-21 can be any natural
      occurring amino acid and up to 18 may be absent
<220> FEATURE:
<221> NAME/KEY: MISC_FEATURE
<222> LOCATION: (24)..(38)
<223> OTHER INFORMATION: His at position 24-38 and up to 13 may be
      absent
<220> FEATURE:
<221> NAME/KEY: MISC_FEATURE
<222> LOCATION: (38)..(38)
<223> OTHER INFORMATION: Pro is optional

<400> SEQUENCE: 15

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Cys His His His His His His His His His
            20                  25                  30

His His His His His Pro
        35

<210> SEQ ID NO 16
<211> LENGTH: 29
<212> TYPE: PRT
<213> ORGANISM: Artificial Sequence
<220> FEATURE:
<223> OTHER INFORMATION: Linker sequence
<220> FEATURE:
<221> NAME/KEY: MISC_FEATURE
<222> LOCATION: (8)..(27)
<223> OTHER INFORMATION: Xaa at position 8-27 can be any natural
      occurring amino acid and up to 18 may be absent
<220> FEATURE:
<221> NAME/KEY: MISC_FEATURE
<222> LOCATION: (29)..(29)
<223> OTHER INFORMATION: Pro is optional

<400> SEQUENCE: 16

His His His His His His Cys Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Cys Pro
            20                  25

<210> SEQ ID NO 17
<211> LENGTH: 29
<212> TYPE: PRT
<213> ORGANISM: Artificial Sequence
<220> FEATURE:
<223> OTHER INFORMATION: Linker sequence
<220> FEATURE:
<221> NAME/KEY: MISC_FEATURE
<222> LOCATION: (2)..(21)
<223> OTHER INFORMATION: Xaa at position 2-21 can be any natural
      occurring amino acid and up to 18 may be absent
<220> FEATURE:
<221> NAME/KEY: MISC_FEATURE
<222> LOCATION: (29)..(29)
<223> OTHER INFORMATION: Pro is optional

<400> SEQUENCE: 17

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Cys His His His His His His Pro
            20                  25

<210> SEQ ID NO 18
<211> LENGTH: 7
<212> TYPE: PRT
<213> ORGANISM: Artificial Sequence
<220> FEATURE:
<223> OTHER INFORMATION: Linker sequence

<400> SEQUENCE: 18

His His His His His His Pro
1               5

<210> SEQ ID NO 19
<211> LENGTH: 8
<212> TYPE: PRT
<213> ORGANISM: Artificial Sequence
<220> FEATURE:
<223> OTHER INFORMATION: Linker sequence

<400> SEQUENCE: 19

His His His His His His Cys Pro
1               5

<210> SEQ ID NO 20
<211> LENGTH: 13
<212> TYPE: PRT
<213> ORGANISM: Artificial Sequence
<220> FEATURE:
<223> OTHER INFORMATION: Linker sequence

<400> SEQUENCE: 20

His His His His His His Cys Gly Gly Gly Gly Cys Pro
1               5                   10

<210> SEQ ID NO 21
<211> LENGTH: 18
<212> TYPE: DNA
<213> ORGANISM: Artificial Sequence
<220> FEATURE:
<223> OTHER INFORMATION: Linker sequence

<400> SEQUENCE: 21
tgcggtggct gcccgtaa                                               18
```

```
<210> SEQ ID NO 22
<211> LENGTH: 20
<212> TYPE: DNA
<213> ORGANISM: Artificial Sequence
<220> FEATURE:
<223> OTHER INFORMATION: Linker sequence

<400> SEQUENCE: 22
gcggtggcgg ttgcccgtaa                                                 20

<210> SEQ ID NO 23
<211> LENGTH: 24
<212> TYPE: DNA
<213> ORGANISM: Artificial Sequence
<220> FEATURE:
<223> OTHER INFORMATION: Linker sequence

<400> SEQUENCE: 23
tgcggtggcg gtggctgccc gtaa                                            24

<210> SEQ ID NO 24
<211> LENGTH: 24
<212> TYPE: DNA
<213> ORGANISM: Artificial Sequence
<220> FEATURE:
<223> OTHER INFORMATION: Linker sequence

<400> SEQUENCE: 24
tgcggtggcg gtggctgccc gtaa                                            24

<210> SEQ ID NO 25
<211> LENGTH: 11
<212> TYPE: PRT
<213> ORGANISM: Artificial Sequence
<220> FEATURE:
<223> OTHER INFORMATION: Linker sequence

<400> SEQUENCE: 25

His His His His His His Cys Gly Gly Cys Pro
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Linker sequence

<400> SEQUENCE: 26

His His His His His His Cys Gly Gly Gly Cys Pro
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Linker sequence

<400> SEQUENCE: 27

His His His His His His Cys Gly Gly Gly Gly Gly Cys Pro
1               5                   10
```

```
<210> SEQ ID NO 28
<211> LENGTH: 7
<212> TYPE: PRT
<213> ORGANISM: Artificial Sequence
<220> FEATURE:
<223> OTHER INFORMATION: Linker sequence

<400> SEQUENCE: 28

His His His His His His Pro
1               5

<210> SEQ ID NO 29
<211> LENGTH: 23
<212> TYPE: PRT
<213> ORGANISM: Artificial Sequence
<220> FEATURE:
<223> OTHER INFORMATION: Linker sequence
<220> FEATURE:
<221> NAME/KEY: MISC_FEATURE
<222> LOCATION: (2)..(21)
<223> OTHER INFORMATION: Xaa at position 2-21 can be any natural
      occurring amino acid and up to 18 may be absent
<220> FEATURE:
<221> NAME/KEY: MISC_FEATURE
<222> LOCATION: (23)..(23)
<223> OTHER INFORMATION: Pro is optional

<400> SEQUENCE: 29

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Cys Pro
            20

<210> SEQ ID NO 30
<211> LENGTH: 15
<212> TYPE: PRT
<213> ORGANISM: Artificial Sequence
<220> FEATURE:
<223> OTHER INFORMATION: Linker sequence

<400> SEQUENCE: 30

Gly Gly Gly Gly Ser Gly Gly Gly Gly Ser Gly Gly Gly Gly Ser
1               5                   10                  15
```